United States Patent [19]

Speeter

[11] 4,271,124
[45] Jun. 2, 1981

[54] NON-DISPERSIVE INFRARED GAS ANALYZER FOR TESTING GASES CONTAINING WATER-VAPOR

[75] Inventor: Winfried Speeter, Herxheim, Fed. Rep. of Germany

[73] Assignee: Siemens Aktiengesellschaft, Berlin & Munich, Fed. Rep. of Germany

[21] Appl. No.: 14,432

[22] Filed: Feb. 23, 1979

[30] Foreign Application Priority Data

Feb. 24, 1978 [DE] Fed. Rep. of Germany ....... 2808033

[51] Int. Cl.³ .................. G01N 7/00; G01N 27/62; G02B 5/24
[52] U.S. Cl. ........................ 422/68; 422/83; 422/98; 23/232 E; 350/312; 356/416; 250/343; 250/345
[58] Field of Search ............. 422/83, 98, 68; 23/232 R, 232 E; 250/343–345; 350/312; 356/416

[56] References Cited

U.S. PATENT DOCUMENTS

| | | | |
|---|---|---|---|
| 3,021,427 | 2/1962 | Bayly et al. | 250/343 |
| 3,725,702 | 4/1973 | Schaefer | 250/343 |
| 3,925,667 | 12/1975 | Staab | 250/343 |
| 4,065,207 | 12/1977 | Zavitsanos | 350/312 |

*Primary Examiner*—William F. Smith
*Assistant Examiner*—Chris Konkol
*Attorney, Agent, or Firm*—Kenyon & Kenyon

[57] ABSTRACT

Infrared absorption gas analyzer systems are provided with cells containing sulfur hexafluoride $SF_6$ for determining the water vapor content of the gas to be measured. In another embodiment, sulfur hexafluoride is used as a selective filter for removing spectral components from a beam of infrared energy so as to prevent cross sensitivity which interferes with the measurement of other gas components. Electrical signals proportional to the water vapor content may be produced by measuring the increase in gas pressure as infrared energy is absorbed, by use of a diaphragm capacitors. In another embodiment, temperature responsive resistors measure the relative attenuation of the infrared energy as it propagates through respective gas components.

8 Claims, 4 Drawing Figures

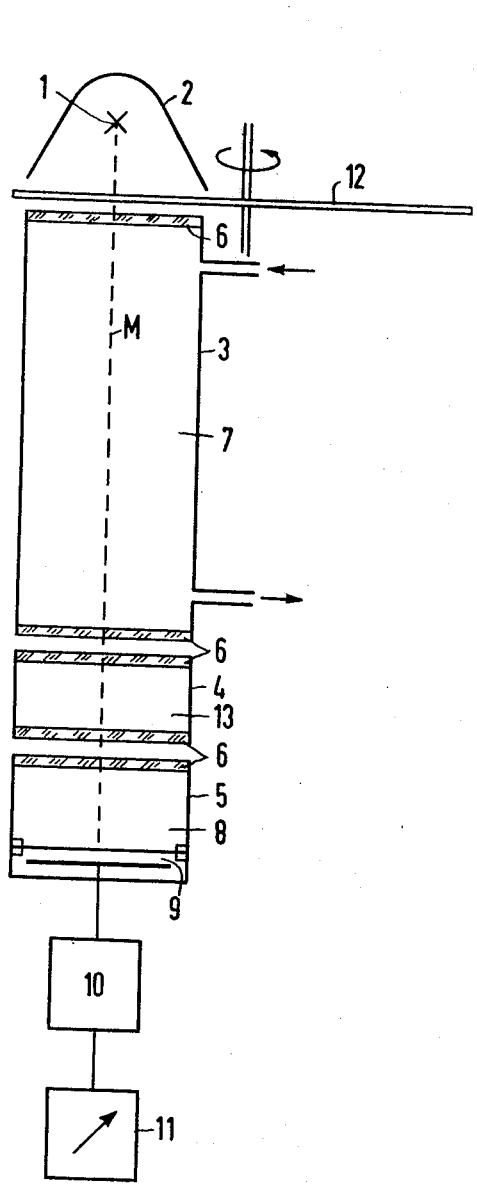
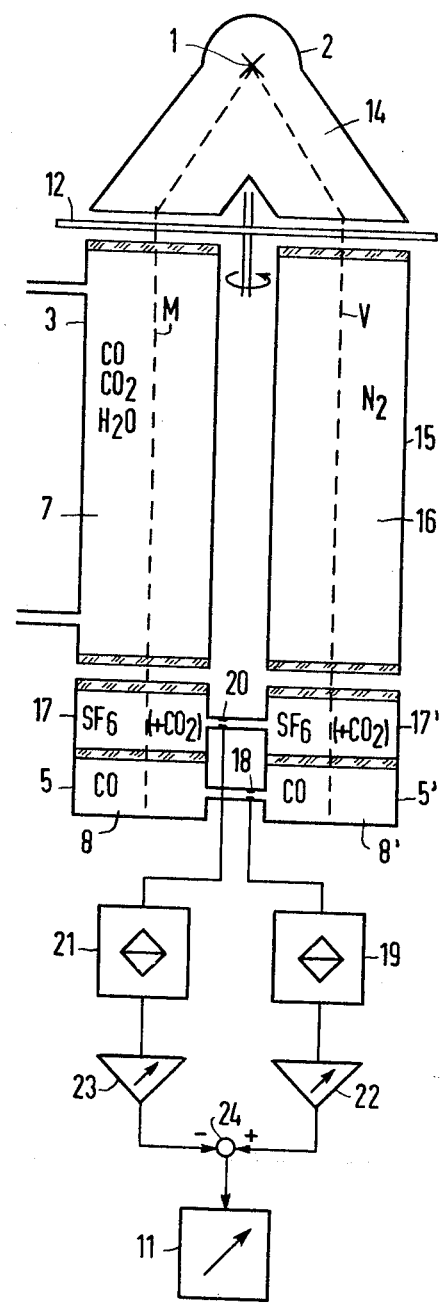
FIG 1
FIG 2

NON-DISPERSIVE INFRARED GAS ANALYZER FOR TESTING GASES CONTAINING WATER-VAPOR

BACKGROUND OF THE INVENTION

This invention relates to systems for measuring the water vapor content of a gas mixture, and more particularly, to systems for suppressing the water vapor cross sensitivity in a non-dispersive infrared absorption gas analyzer.

Infrared absorption gas analyzers operate utilizing a physical property of gases in which the different atomic structures of different gases absorb corresponding spectral regions of infrared radiation. Such absorption of infrared energy by gas contained within a closed volume causes a measureable increase in its temperature and pressure. The concentrations of predetermined gaseous components within a gas mixture can be determined from temperature and pressure measurements.

A typical prior art system for obtaining the desired temperature and pressure measurements utilizes a source of infrared radiation which transmits electromagnetic energy in the infrared range through a measurement cell which contains a sample of the gas mixture which is to be examined, and a receiver chamber which contains a sample of the gas component, either in pure form or mixed with other gases, of the type which is desired to be measured. The measurement cell and the receiver chamber, which are each disposed in the path of the infrared energy, contain windows of a material which is transparent in the infrared spectral region, typically having wavelengths in the range between 2 and 10 microns, so as to permit the energy to propagate through the various gases.

It is a problem in the art that the gas mixture contained in the measurement cell contains gaseous components which cause "cross sensitivities". Such cross sensitivities may be caused by water vapor contained in the measurement gas, which interferes with the measurement of other gaseous components. It is desirable to eliminate the interfering component by interposing a filter cell, which is commonly filled with a filter gas corresponding to the interfering component, and which is disposed in the radiation path so as to absorb the particular interfering spectral components from the radiation. Alternatively, in the case of water vapor, it may be desirable to measure the water vapor component by filling the receiver chamber with water vapor. Thus, infrared radiation which passes through the gaseous mixture in the measurement cell would also propagate through the receiver chamber, affect the thermodynamic state of the water vapor in the receiver chamber, and such changes could be converted to electrical signals for measuring the water vapor content of the gaseous mixture in the measurement cell. The problem arises that it is difficult to contain water vapor in either a receiver chamber or in a filter cell because of its instability at ambient temperatures. Water vapor has a relatively low dew point and will tend to absorb the infrared radiation as a function of its temperature.

It is therefore an object of this invention to provide a gas which absorbs infrared energy in wavelength bands which correspond to those of water vapor, and which is chemically stable at ambient temperatures.

It is a further object of this invention to provide a stable gas which has an infrared absorption characteristic similar to that of water vapor, and which is not in general use as a gas to be measured.

It is another object of this invention to provide a gas which can be mixed with other non-absorbing filter gases such as nitrogen or argon, or with another absorbing gas, such as carbon dioxide.

SUMMARY OF THE INVENTION

The foregoing and other problems in the art are alleviated by using sulfur hexafluoride $SF_6$ as a gas for selectively filtering spectral components corresponding to water vapor, or as a reference gas in a receiver chamber for determining the water vapor component in a gas mixture to be measured.

In some embodiments of the invention, sulfur hexafluoride can be used as a substitute for water vapor. It can be mixed with other gases in predetermined proportional quantities, so as to achieve a predeterminable partial pressure of sulfur hexafluoride in a filter gas. As indicated, such additional component gases may be of a type which do not absorb infrared radiation, such as nitrogen or argon, or may by of a type which absorb a predetermined interference component in the infrared spectrum, such as carbon dioxide. The selective filtering effect of sulfur hexafluoride may be advantageously adjustable in response to its partial pressure in the gas mixture.

A known infrared gas analyzer system which may benefit from the use of this invention is shown in German Pat. reference No. 1 109 148. In this reference, two spectrally selective radiation receivers are provided, and are disposed behind one another in the path of an infrared energy beam. The infrared radiation receivers are disposed on the other side of a measuring cell from a source of infrared radiation. The receivers are in the form of radiation-permeable, gas-filled chambers, which are provided with means for converting variation in the pressure or temperature of the gas resulting from the absorption of the infrared energy into responsive electrical output signals. The respective responsive output signals are combined in a difference circuit. In one embodiment of the invention, one of the radiation receivers is filled with sulfur hexafluoride, and the other radiation receiver is filled with the component gas to be measured. The output signal of the radiation receiver filled with sulfur hexafluoride is weighted with a percentage factor and electrically combined in the difference circuit so as to tend to counteract the output signal of the other radiation receiver. Such a differential combination of output signals compensates for water vapor cross sensitivity. Although this technique for electrically suppressing the interfering spectral component requires an increase in the cost of circuitry over known systems, such increased cost is outweighed by the advantage that the influence of water vapor as an interfering spectral component is more easily suppressed than by the careful predetermination of the partial pressure of sulfur hexafluoride in the receiver chamber, or in a filter cell.

BRIEF DESCRIPTION OF THE DRAWINGS

Comprehension of the invention is facilitated by reading the following detailed description in conjunction with the annexed drawings in which:

FIG. 1 depicts an infrared gas analyzer, partly in schematic form and partly in block and line representation, which operates in accordance with a single beam alternating light method;

FIG. 2 shows an infrared gas analyzer, partly in schematic form and partly in block and line representation, which operates in accordance with a double beam alternating light method;

DETAILED DESCRIPTION

Figure 3:
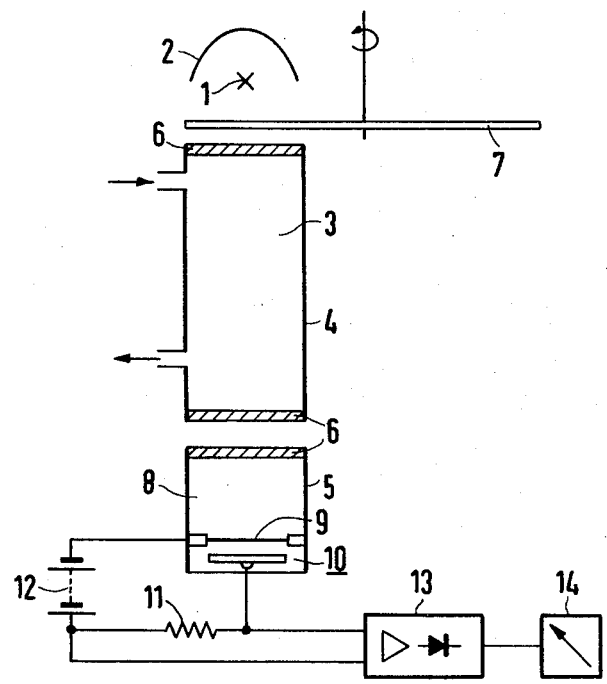
FIG. 3 shows an infrared gas analyzer system, partly in schematic form and partly in block and line representation, which utilizes a single alternating beam with a selective receiver.

FIG. 1 shows an infrared gas analyzer which operates in accordance with the known single-beam alternating-light method. An infrared radiation source 1 is disposed within a reflector 2, so as to direct the infrared radiation along a path M. A measuring cell 3, a filter cell 4 and a receiver chamber 5 are sequentially disposed along path M. The end faces of measuring cell 3 and filter cell 4, and one end face of receiver chamber 5 are provided with windows 6 which are of an infrared transparent material, illustratively, calcium fluoride.

In operation, measurement cell 3 is filled with a measurement gas 7 which may be composed of a variety of gaseous components, including water vapor; measurement gas 7 being circulated through measuring cell 3 as shown by the directional arrows at the inlet and outlet of the measuring cell. The particular component of the measuring gas mixture 7, which is to be determined quantitatively, is present in either a pure form or mixed with non-absorbing gases as reference gas 8 in receiver chamber 5.

An increase in the pressure of the reference gas 8 resulting from the absorption of infrared radiation is transformed into a responsive electrical signal by a pressure transducer which, in this embodiment of the invention, is in the form of a diaphragm capacitor 9. Diaphragm capacitor 9 is connected to a circuit 10 which is coupled at its output to an indicating device 11. Indicating device 11 produces an indication which is responsive to the pressure of reference gas 8 in receiver chamber 5. Since diaphragm capacitor 9 and its associated circuitry will more easily process an alternating signal, the infrared energy propagating along path M is periodically interrupted by means of a rotating shutter 12.

It is a problem with this technique for measuring a component of measurement gas mixture 7 that, as a result of water vapor contained in gas mixture 7, the absorption spectrum of gas mixture 7 often overlaps the absorption spectrum of reference gas 8 in receiver chamber 5. Such spectrum overlap produces error in the output signal indicated at indicator 11, which should otherwise be proportional to only the unknown component of the measurement gas 7. In this embodiment, a filter gas 13, which is contained in filter cell 4, is used to filter out the important absorption bands of water vapor in the wavelength region between 2 and 10 microns. Filter gas 13 contains sulfur hexafluoride which may be alone, in combination with additional non-absorbing gases, or with other absorbing gases which are intended to filter out other spectral components.

FIG. 2 shows an infrared gas analyzer which operates in accordance with the two-beam alternating-light method. An infrared radiation source 1 is disposed within a reflector 2, the output beam of which is divided by beam divider 14 into two parallel ray paths, M and V. The propagation of infrared energy along paths M and V is alternatingly interrupted by rotating shutter 12. Measuring cell 3 containing a measurement gas 7, and receiver chambers 17 and 5 are disposed sequentially along path M. Reference cell 15 containing reference gas 16, and radiation receivers 17' and 5' are sequentially disposed along path V. In this embodiment, measurement gas 7 may consist of carbon monoxide, carbon dioxide and water vapor. Reference gas 16 may be a non-absorbing gas such as nitrogen $N_2$. Receiver chambers 5 and 5' are each filled with carbon monoxide CO, which is the particular component of measurement gas 7 to be quantitatively determined. Receiver chambers 5 and 5' communicate with one another by means of a line, in which is disposed a thermal flow sensor 18. Thermal flow sensor 18 is connected to a measuring bridge circuit 19. Receiver chambers 17 and 17' are filled with a combination of sulfur hexafluoride $SF_6$ and carbon dioxide $CO_2$ so as to absorb the energies corresponding to the energy spectrum of interfering components carbon dioxide and water vapor $H_2O$ of the measurement gas 7. Pressure variations are detected by thermal flow sensor 20 which is arranged in a connection between chambers 17 and 17', which is connected to a second measuring birdge circuit 21.

Measuring bridge circuits 21 and 19 are each connected to a respective one of adjustable gain amplifiers 22 and 23. The output signals of amplifiers 22 and 23 are subtractively combined in subtractor 24 which is connected at its output to an indicator 11. The output signal of subtractor 24, which is represented in amplitude by indicator 11, is proportional to the carbon monoxide CO content in measurement gas 7. The gain of amplifier 22 is advantageously adjusted so as to determine a null point of indicator 11 and the range of measurement. The gain of amplifier 23 is adjusted to determine the proportion of compensation signal for the interfering components, especially for water vapor, which may vary over a large range.

FIG. 3 shows an infrared absorption gas analyzer which operated according to the single-beam alternating-light method with a selective receiver. An infrared radiation source 1 is disposed within a reflector 2 so as to direct a beam of electromagnetic infrared energy through a measuring cell 4 which is filled with a measurement gas 3, and a receiver chamber 5. Measurement gas 3 contains water vapor which is to be quantitatively determined. Receiver chamber 5 contains pure sulfur hexafluoride alone or mixed with nitrogen or a rare gas. As previously noted, measuring cell 4 and receiver chamber 5 are sealed at the ends with calcium fluoride windows 6.

Selected spectral portions of the infrared energy which enters receiver chamber 5 are absorbed by gas 8 which increases in temperature and pressure, so as to deflect diaphragm 9 of diaphragm capacitor 10. As indicated, the infrared energe beam is periodically interrupted by rotating shutter 7 so as to produce alternating pressure variations which are converted into an alternating electrical signal at a resistor 11 which is connected to diaphragm capacitor 10, and a power supply flow. The alternating signal is amplified and rectified by a signal processing stage 13 which produces an output signal corresponding to the water vapor content of measurement gas 3, and which is indicated by measuring instrument 14. In similar manner, this embodiment of the invention may be incorporated into a known two-beam gas analyzer having a reference path, such as that described hereinabove with respect to FIG. 2.

Figure 4:
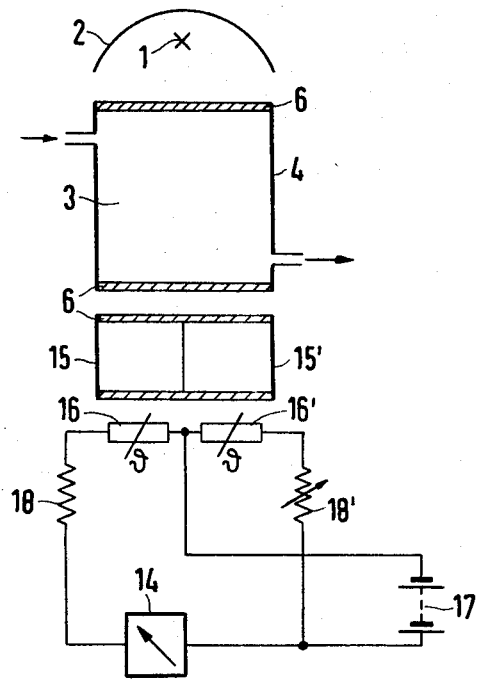
FIG. 4 shows an infrared gas analyzer, partly in schematic form and partly in block and line representation, utilizing a non-selective receiver and subtractive filtering.

FIG. 4 shows a gas analyzer having a non-selective receiver and subtractive filtering. The infrared energy produced by infrared source 1 is directed by reflector 2 so as to propagate through measuring cell 4 and through two cells 15 and 15' which are disposed in parallel. A measurement gas 3 is circulated through measurement cell 4. Cell 15 may contain a gas with sulfur hexafluoride, while cell 15' contains other gas components of the measurement gas 3, or a non-absorbing gas.

The radiation energy which propagates through cells 15 and 15' contacts non-selective radiation receivers in the form of temperature responsive resistors 16 and 16', which are connected in a difference circuit with a power supply 17. The current flowing through resistors 16 and 18 correspond to the water vapor content of measurement gas 3. Resistor 18' may be advantageously adjusted to preselect the null point of an indicating instrument 14, and the ratio of the total absorptions of water vapor and sulfur hexafluoride with respect to other gas components.

Although the inventive concept disclosed herein has been described in terms of specific embodiments and applications, other applications and embodiments will be obvious to persons skilled in the pertinent art without departing from the scope of the invention. The drawings and descriptions of specific embodiments of the invention in this disclosure are illustrative of applications of the invention and should not be construed to limit the scope thereof.

I claim:

1. A non-dispersive infrared gas analyzer for detecting a predetermined component of a first gas mixture which is free of sulfur hexafluoride, one such component gas the gas analyzer being of the type which contains a source of infrared radiation for producing a beam of infrared radiation and a measurement cell for holdng the first gas mixture in the path of the beam of infrared radiation;

CHARACTERIZED IN THAT there are further provided
   (a) a first chamber disposed in the path of the beam of infrared radiation containing a second gas containing sulfur hexafluoride, said sulfur hexafluoride having an infrared energy absorption characteristic corresponding to that of water vapor, so as to absorb energy from said beam of infrared radiation in preselected spectral energy bands; and
   (b) detector means responsive to said beam of infrared radiation for producing an electric signal responsive to variations in the beam of infrared radiation.

2. The non-dispersive infrared gas analyzer of claim 1 wherein there is further provided
   (a) a second chamber disposed in the path of the beam of infrared radiation, said first chamber being interposed between said second chamber and the source of infrared radiation, for holding a third gas containing a preselected component gas of the first gas mixture.

3. The non-dispersive infrared gas analyzer of claim 2 wherein said detector means comprises a diaphragm capacitor having a diaphragm for moving in response to variations in the pressure of said third gas in said second chamber.

4. The non-dispersive infrared gas analyzer of claim 1 wherein said detector means comprises a diaphragm capacitor having a diaphragm for moving in response to variations in the pressure of said second gas in said first chamber.

5. The non-dispersive infrared gas analyzer of claim 1 wherein there is further provided
   (a) a third chamber disposed in the path of the beam of infrared radiation, and in parallel with said first chamber, with respect to the beam of infrared radiation, for holding a fourth gas, said fourth gas having a predetermined infrared energy absorption characteristic.

6. The non-dispersive infrared gas analyzer of claim 5 wherein said detector means comprises
   (a) first sensor means for producing an electrically measureable condition responsive to a first portion of said beam of infrared radiation which propagates through said first chamber,
   (b) second sensor means for producing an electrically measureable condition responsive to a second portion of said beam of infrared radiation which propagates the said third chamber, and
   (c) difference circuit means for producing a difference signal responsive to the difference between the respective electrically measureable conditions produced by said first and second sensor means.

7. A non-dispersive infrared gas analyzer for detecting a predetermined component of a first gas mixture which is free of sulfur hexafluoride, the gas analyzer being of the type which contains a source of infrared radiation for producing a beam of infrared energy, and a cell for holding the first gas mixture in the path of the beam of infrared energy;

CHARACTERIZED IN THAT there are further provided
   (a) a first chamber containing a second gas containing sulfur hexafluoride in the path of the beam of infrared energy;
   (b) a second chamber for holding a third gas containing a predetermined component gas of the first gas mixture in the path of the beam of infrared energy; and
   (c) detector means in said first chamber responsive to variations in selected thermodynamic parameters in said second gas, the variations being responsive to the infrared energy which is absorbed.

8. A non-dispersive infrared gas analyzer for detecting a predetermined component of a first gas mixture which is free of sulfur hexafluoride, the gas analyzer being of the type which contains a source of infrared radiation for producing a beam of infrared energy, and a cell for holding the first gas mixture in the path of the beam of infrared energy;

CHARACTERIZED IN THAT there are provided
   (a) a first chamber containing a second gas containing sulfur hexafluoride in the path of the beam of infrared energy;
   (b) a second chamber for holding a third gas containing a predetermined component gas of the first gas mixture in the path of the beam of infrared energy; and
   (c) detector means in said second chamber responsive to variations in selected thermodynamic parameters in said third gas, the variations being responsive to the infrared energy which is absorbed.

* * * * *